United States Patent [19]

Andrei et al.

[11] Patent Number: 5,501,920
[45] Date of Patent: Mar. 26, 1996

[54] SOLID POLYMERIC ELECTROLYTE INCLUDING A CROSS-LINKED POLYETHER ENCOMPASSING AN ION COMPOUND AND A LIQUID PLASTICIZER

[75] Inventors: Maria Andrei, Berceto; Arnaldo Roggero, San Donato Milanese; Massimo Soprani, Borgosesia; Alberto Gandini, Milan, all of Italy

[73] Assignee: Eniricerche S.p.A., Milan, Italy

[21] Appl. No.: 267,521

[22] Filed: Jun. 29, 1994

[30] Foreign Application Priority Data

Jul. 9, 1993 [IT] Italy .................................. MI93A1488

[51] Int. Cl.⁶ ..................................................... H01M 6/18
[52] U.S. Cl. ............................................. 429/192; 252/62.2
[58] Field of Search .............................. 429/192; 252/62.2

[56] References Cited

U.S. PATENT DOCUMENTS

| | | | |
|---|---|---|---|
| 4,886,716 | 12/1989 | Roggero et al. | 429/192 |
| 5,138,013 | 8/1992 | Mason. | |
| 5,173,205 | 12/1992 | Marchese et al. | 429/192 X |
| 5,264,307 | 11/1993 | Andrei et al. | |
| 5,411,819 | 5/1995 | Marchese et al. | 429/192 |

FOREIGN PATENT DOCUMENTS 0492710  7/1992  European Pat. Off. .
0499115  8/1992  European Pat. Off. .

Primary Examiner—John S. Maples
Attorney, Agent, or Firm—Oblon, Spivak, McClelland, Maier, & Neustadt

[57] ABSTRACT

A solid polymeric electrolytic membrane comprising a solution of an ion compound in a cross-linked polyether including a liquid plasticizer obtained by:

a) copolymerizing a vinyl ether of the formula:

$$R-(O-CH_2-CH_2-)_n-O-CH=CH_2 \qquad (I)$$

with an allyl vinyl ether of the formula:

$$CH_2=CH-CH_2-(O-CH_2-CH_2-)_m-O-CH=CH_2 \qquad (II)$$

where R is a methyl or ethyl radical, n is an integer ranging from 1 to 16, m is an integer ranging from 1 to 10 and the molar ratio of (I) to (II) is between 70/30 and 95/5, forming an allyl copolymer; b) hydrosilating the allyl double bonds of the allyl copolymer by reaction with trimethoxy or triethoxy silane to form a hydrosilated copolymer; c) cross-linking the hydrosilated copolymer by means of a diprotic cross-linking agent in a plasticizer solution of an oligomer or a dipolar aprotic solvent present in a quantity of 20 to 80% by weight and in the presence of an ion compound, and evaporating the low-boiling compounds formed in step c) to obtain a membrane capable of retaining the liquid plasticizer.

11 Claims, 2 Drawing Sheets

SOLID POLYMERIC ELECTROLYTE INCLUDING A CROSS-LINKED POLYETHER ENCOMPASSING AN ION COMPOUND AND A LIQUID PLASTICIZER

The present invention relates to a solid polymeric electrolyte based on polyether, a procedure for its preparation and its use in electrochemical devices.

Solid polymeric electrolytes, also called ion conducting polymers, are known in the art, composed of a solution of an ion compound completely dissolved in a solid plastic macromolecular material, the latter being the polymerization product of monomers containing at least one hetero-atom, especially oxygen.

This macromolecular material is generally polyethylenoxide (PEO), or other polyethers described in U.S. Pat. No. 4,471,037, French patents 2.523.769, 2.568.574, EP-13037 and EP-13199.

The problems connected with these solid polymeric electrolytes generally consist in the fact that they only have a satisfactory ion conductivity at temperatures higher than room temperature, with a limited mechanical resistance and dimensional stability of the corresponding electrolytic membranes. All this makes the solid polymeric electrolytes of the known art of little interest for practical use.

Solid polymeric electrolytes based on polyvinylethers, characterized by a good mechanical resistance and satisfactory ion conductivity at low temperatures, have recently been described in U.S. Pat. Nos. 4,886,716 and 5,173,205.

The preparation of these electrolytes requires a procedure with several steps which include the dissolution of the solid polyvinylether in a suitable solvent, preferably acetonitrile, containing an ion compound and, possibly a chemical activator to induce cross-linking, and finally the evaporation of the solvent in order to obtain a membrane.

It is now been found, according to the present invention, that membranes with an excellent mechanical resistance and improved ion conductivity compared to the polymers of the known art can be obtained by dissolving the polymer based on polyvinylether and the ion compound in a high-boiling plasticizer. The crosslinking reaction with a chemical agent capable of reacting, at room temperature, with the Si—OEt groups present in the matrix by generating cross-linking points of the type Si—O—Si enables the production of a membrane capable of encompassing an active plasticizer.

BRIEF DESCRIPTION OF THE DRAWINGS

In FIG. 1 the curves have the following meaning:

Figure 1:
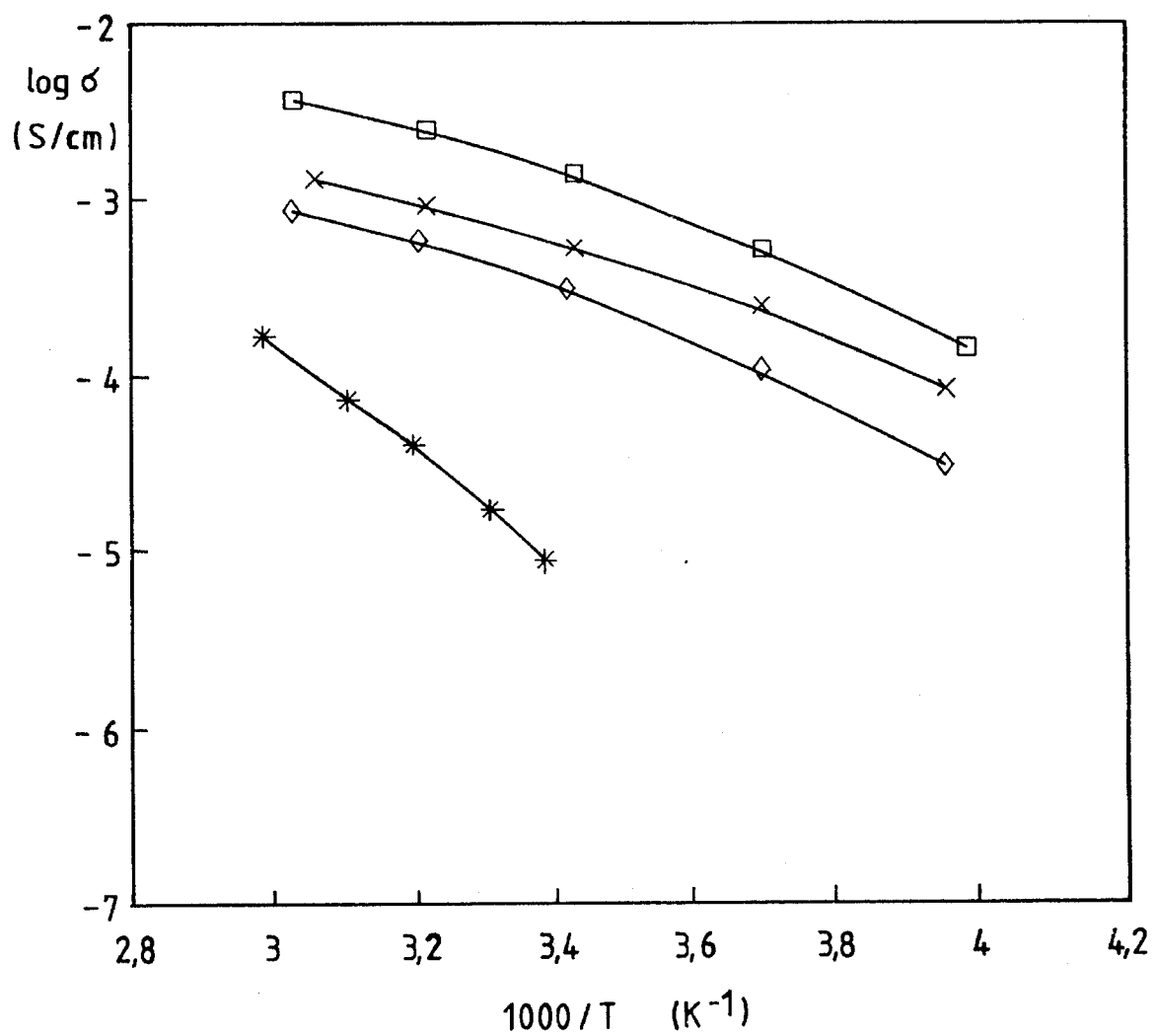
FIGS. 1 and 2 show the behavior of the conductance in relation to the temperature.

*: PVE-SIL; □: PVE-SIL1; ◊: PVE-SIL2; X: PVE-SIL3. Likewise, in FIG. 2 the curves have the following meaning:

*: PVE-SIL4; ◊: PVE-SIL5.

In accordance with this, the first aspect of the present invention relates to a solid polymeric electrolyte, in the form of a membrane, composed of a solid solution of an ion compound dissolved in a crosslinked polyether, characterized in that said electrolyte is obtained: a) by copolymerizing a vinyl ether having the formula:

$$R-(O-CH_2-CH_2-)_nO-CH=CH_2 \quad (I)$$

wherein: R indicates the methyl or ethyl radical; n is an integer varying from 1 to 16 with an allyl vinyl ether having the formula:

$$CH_2=CH-CH_2-(O-CH_2-CH_2-)_m-O-CH=CH_2 \quad (II)$$

wherein: m is an integer varying from 1 to 10, with a molar ratio between (I) and (II) of between 70/30 and 95/5, to obtain a copolymer having allyl unsaturations; b) by hydrosilylating the double allyl bond of the copolymer obtained in step (a) by reaction with an alkoxy silane selected from trimethoxy and triethoxy silane, to obtain a hydroxylated copolymer; c) by cross-linking the hydrosilylated copolymer obtained in step (b) by means of a diprotic crosslinking agent operating in solution in a plasticizer, selected from an oligomer or a dipolar aprotic solvent in a quantity of 20 to 80% by weight, in the presence of an ion compound and evaporating the low-boiling compounds formed in the cross-linking reaction to obtain a membrane capable of encompassing the active plasticizer.

In step (a) of the present invention a copolymer is prepared by the cationic polymerization of a vinyl ether (I) and an allyl vinyl ether (II), in the above molar ratios.

The vinyl ether (I) can be prepared by the reaction of ethyl vinyl ether with a polyoxyethylene glycol mono-methyl or ethyl ether. The monomer (II) can be obtained by reaction between vinyl ether with an ethylene chlorohydrin (in turn obtained by the transvinylation of the ethylene chlorohydrin) and allyl alcohol operating in a solvent such as dimethylsulphoxide, in the presence of a base such as potassium hydroxide, at a temperature of about 80° C. The monomers (I) and (II) are obtained with a purity of higher than 99% using the conventional separation techniques.

The copolymerization reaction is carried out in an inert solvent at a temperature of about −75°/−80° C. and in the presence of a Friedel-Crafts catalyst used in a quantity of 0.8 to 1.0 moles for every 100 moles of monomers (I) and (II).

Examples of catalysts suitable for the purpose are boron etherate trifluoride, aluminium trichloride, halides of aluminium alkyl and tin tetrachloride. Examples of solvents suitable for the purpose are chlorinated solvents such as dichloromethane and hydrocarbons such as toluene, benzene, heptane. Under the above conditions the polymerization times are about 1–3 hours.

At the end of the polymerization the catalyst is deactivated by adding an aliphatic alcohol such as methanol. The copolymer is then recovered, using the conventional separating techniques, in the form of a colourless viscous liquid with a weight average molecular weight of about 20,000–100,000, depending on the polymerization temperature, and a glass transition temperature, determined by DSC, within the range of −65° C. and −80° C.

The copolymer thus obtained can be characterized by analytic techniques such as NMR and FT-IR. The results of these analyses confirm the absence of the double vinyl bond and the presence of the double allyl bond in the same percentage initially introduced.

In step (b) of the present invention the allylic function of the copolymer is subjected to hydrosilylation by reaction with an alkoxy silane selected from trimethoxy and triethoxy silane. In this way the allylic function in the copolymer is transformed into a function having the formula:

$$(R'O)_3Si-CH_2-CH_2-CH_2-((O-CH_2-CH_2-)_m-O-P$$

wherein

R' indicates the methyl or ethyl group;

P schematically indicates the polymer and m has the meaning defined above.

More specifically the copolymer, carefully dried, is functionalized with a trialkoxy silane operating in an inert and anhydrous solvent, at a temperature of about 80°–100° C.

and in the presence of a catalyst containing a transition metal, added in concentrations of ppm (parts per million). Examples of solvents suitable for the purpose are hydrocarbons such as toluene, benzene, heptane, hexane and cyclohexane. Examples of catalysts suitable for the purpose are hexachloroplatinic acid, triphenylphosphine rhodium chloride, dicobalt octacarbonyl. The functionalization of the copolymer is verified by $^1$H and $^{13}$C nmr spectroscopy, after removing the solvent and excess trialkoxy silane under vacuum.

In step (c) of the present invention the hydrosilylated copolymer is dissolved in a plasticizer containing an ionic compound dissolved therein and then cross-linked by means of suitable diprotic products, such as cross-linking agents, to generate siloxanic bridges of the —Si—O—Si— type.

The cross-linking agent is preferably an ethylene glycol acidulated with HCl and added in a quantity of about 40–200 microlitres per gram of copolymer in relation to the quantity in moles of comonomer (II).

The ionic compounds suitable for the purpose of the present invention are salts, preferably perchlorates, borates, fluoroborates, thiocyanates, hexafluoro arseniates, trifluoroacetates and trifluoromethansulphonates of metals (monovalent or polyvalent) and especially lithium, sodium, potassium, calcium, copper, zinc, magnesium, lead, tin and aluminium. Preferable for the purpose are the salts of lithium and especially lithium perchlorate, and in this case it is used in a quantity of between 1 and 30% by weight, preferably in a quantity of about 3–10% by weight. Plasticizers suitable for the purpose of the present invention can be selected from oligomers containing ethylene oxidic chains or aprotic dipolar solvents with a high dielectric constant, low volatility and dissociant properties with respect to the lithium salts.

Examples of these oligomers are oligoethylene glycol dialchylethers (Diglime, triglime, tetraglime) and polyethylene glycol dialkylethers with a low molecular weight (PEGME). Examples of the solvents are propylen carbonate (PC), ethylen carbonate (EC), gammabutyrolactone, dimethoxyethane (DME) and their mixtures.

According to a preferred embodiment a plasticizer is present in the mixture in a quantity of between 20 and 80% by weight, preferably between 30 and 70%.

In particular in the embodiment of step (c), the ionic compound and hydrosilylated copolymer can be dissolved in a plasticizer selected from those listed above. The cross-linking agent is then added to the homogeneous solution in a quantity of about 3 times in moles with respect to the equivalents of reagents on the silane. The homogeneous solution thus obtained is then poured into a suitable mould, preferably made of teflon, and kept at room temperature until complete cross-linking has taken place (about 4–8 hours).

The low-boiling components, which are formed as byproducts of the cross-linking reaction, are then removed by treatment under vacuum.

The membrane thus obtained has an excellent mechanical consistency, it is transparent-and has a thickness of about 100 μm.

The polymeric electrolyte thus obtained has a glass transition temperature of between −100° C. and −60° C. depending on the composition of the mixture.

The polymeric electrolyte of the present invention is mechanically resistant, dimensionally stable and highly conductive even at low temperatures. The solid polymeric electrolyte can be used as an electrolytic separator in electrochemical devices, in optical displays and in sensors.

The following examples are illustrative and do not limit the scope of the present invention in any way.

EXAMPLE 1

Preparation of Vinyl Ether

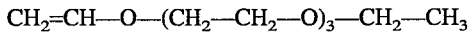

Ethyl vinyl ether (1.8 moles), triethyleneglycol monoethyl ether (0.6 moles) and mercury acetate (5.7× 10$^{-3}$ moles) are charged into a three-necked, 500 ml flask equipped with a reflux cooler and maintained under a nitrogen flow. The mixture is heated to reflux temperature and is kept under reflux conditions for 10 hours.

During this period the temperature rises from its initial value of 39° C. to the final value of 42° C. The reaction is then blocked to add solid potassium carbonate and the mixture is distilled, first at atmospheric pressure, to eliminate the excess ethyl vinyl ether and ethyl alcohol which is the reaction byproduct, and then at reduced pressure (20 mm Hg) to separate the vinyl ether in the titer from the unchanged glycol monoethylether.

The vinyl ether thus produced has a purity higher than 99% and its yield, with respect to the triethylene glycol monoethyl ether at the start, is equal to about 80%. Its structure is confirmed by NMR and IR spectroscopy, and by mass spectrometry.

EXAMPLE 2

Preparation of Allyl Vinyl Ether 250 ml of dimethylsulphoxide, 55 g (982 mmoles) of ground potassium carbonate and 34 ml (500 mmoles) of distilled allyl alcohol are charged into a three-necked 500 ml glass flask, equipped with a reflux cooler, mechanical stirrer and kept under a nitrogen flow. The mixture is left under stirring for 1 hour, and then 62.5 g (415 mmoles) of vinyl ether of diethylene chlorohydrin are slowly added dropwise. At the end of the addition the reaction mixture is heated to 80° C. for 2 hours. The resulting mixture is poured into cold water (about 500 ml) and is extracted with three 250 ml portions of chloroform; the joint organic phases are washed with water until they become neutral and then dried with anhydrous sodium sulphate. The chloroform is removed by means of the rotating evaporator, and the reaction raw product, about 40 g of yellowish oil, is distilled under vacuum (0.01 mm Hg), obtaining 30 g of pure allyl vinyl ether (colourless liquid). The structure is confirmed by mass, FT-IR, $^1$H and $^{13}$C nmr spectrometry.

EXAMPLE 3

Copolymerization of Vinyl Ether and Allyl Vinyl Ether 30.0 mmoles of vinyl ether of example 1 and 1.5 mmoles of allyl vinyl ether of example 2 dissolved in 20 ml of anhydrous methylene chloride are charged into a 50 ml glass reactor, equipped with a helical mechanical stirrer and inlets for nitrogen and the charging of the reagents. The mixture is cooled to −78° C., and 0.32 mmoles of etherified BF$_3$ dissolved in 2 ml of anhydrous methylene chloride are then rapidly added under vigorous stirring.

After about 2 hours there is a considerable increase in the viscosity accompanied by a clouding of the solution. The polymerization is then interrupted and an excess of methanol (2 ml) added; the mixture is left to reach room temperature, and methylene chloride is then added and is poured into 200 ml of water and bicarbonate; the organic phase is separated and is then washed with water and finally dried on anhydrous sodium sulphate. After removing the solvent and treatment under vacuum (0.01 mmHg) at 60° C., a colourless sticky product is obtained; the yield is quantitative.

The copolymer is characterized by NMR and FT-IR spectroscopy confirming the presence of the allyl function bound to the polymer, in the same percentage as the beginning, and the absence of the double vinyl bond. In addition, DSC analysis confirms that the polymer is amorphous ($T_g = -77°$ C.).

EXAMPLE 4

Silylation of the copolymer

The solution of copolymer (5 grams in 20 ml of anhydrous toluene), obtained according to the procedure of example 3, is poured into a 50 ml tailed test-tube, in a nitrogen atmosphere, triethoxysilane (6.25 mmoles) in excess with respect to the molar content of double bonds (4:1) is then added. Finally, 30 microlitres of hexachloroplatinic acid ($H_2PtCl_6$) at 3.3% in isopropanol are added to the solution. The reactor is hermetically closed with a blind nipple and the nitrogen flow is also interrupted. The reaction is carried out, under stirring, at 110° C. for 7 hours, room temperature is then restored and the mixture is transferred by siphoning, under a nitrogen flow, to a 250 ml flask. The solvent and excess triethoxysilane are removed under vacuum (0.01 mm Hg) by heating to 45° C. for about 7 hours. The copolymer (indicated as COP-SIL) has the same appearance as the starting material and is only slightly yellow-coloured. Characterization by means of NMR and FT-IR confirms the disappearance of the allyl double bonds, the absence of Si—H groups and the presence of Si—O—Et groups. In addition, DSC analysis confirms that the polymer is amorphous ($T_g = -79°$ C.).

EXAMPLES 5–9

Preparation of Electrolytic Membranes

Electrolytic membranes, based on polyether, are prepared in a glove-box, in an argon atmosphere and with a degree of humidity lower than 10 ppm operating as follows:

$LiClO_4$ is dissolved in a plasticizer and the solution is homogenized at room temperature for a night;

the silylated polyvinylether of example 4 (COP-SIL) and a small quantity (20 μl) of diethylenglycol slightly acidified with HCl are added to this solution and the mixture is homogenized at room temperature;

the solution obtained is poured into circular teflon moulds having a diameter of 3 cm and a thickness of 200 μm and the low-boiling components (ethanol) which are formed as by-products of the cross-linking reaction, are removed by treatment under vacuum (50 mm Hg). The cross-linking is complete after about 4–8 hours. FT-IR analysis of the membranes shows the absence of absorptions caused by unreacted SiOEt groups and the appearance of absorptions of the type Si—O—Si. Table 1 below shows the plasticizers and quantities used for the preparation of the membranes.

TABLE 1

| TYPE | COP-SIL mg | COP-SIL % w/w | PLASTICIZER Type | PLASTICIZER mg | PLASTICIZER % w/w | Li ClO4 mg | Li ClO4 % w/w | Tg (°C.) |
|---|---|---|---|---|---|---|---|---|
| PVE-SIL1 | 400 | 47 | PC | 400 | 47 | 50 | 6 | −87 |
| PVE-SIL2 | 400 | 47 | TGME | 400 | 47 | 50 | 6 | −92 |
| PVE-SIL3 | 400 | 47 | TGME/ DGME | 200 200 | 23.5 23.5 | 50 | 6 | −91 |
| PVE-SIL4 | 400 | 31 | TGME | 800 | 63 | 77 | 6 | −102 |
| PVE-SIL5 | 400 | 31 | PC | 800 | 63 | 73 | 6 | −104 |

The measurement of the conductance of the membranes is carried out in a cell equipped with two symmetrical carbon-steel electrodes, between which the membrane is compressed, by applying an alternate sinusoidal potential drop with an amplitude equal to 100 mV. The glass transition temperature of the membranes is determined by DSC.

Figure 2:
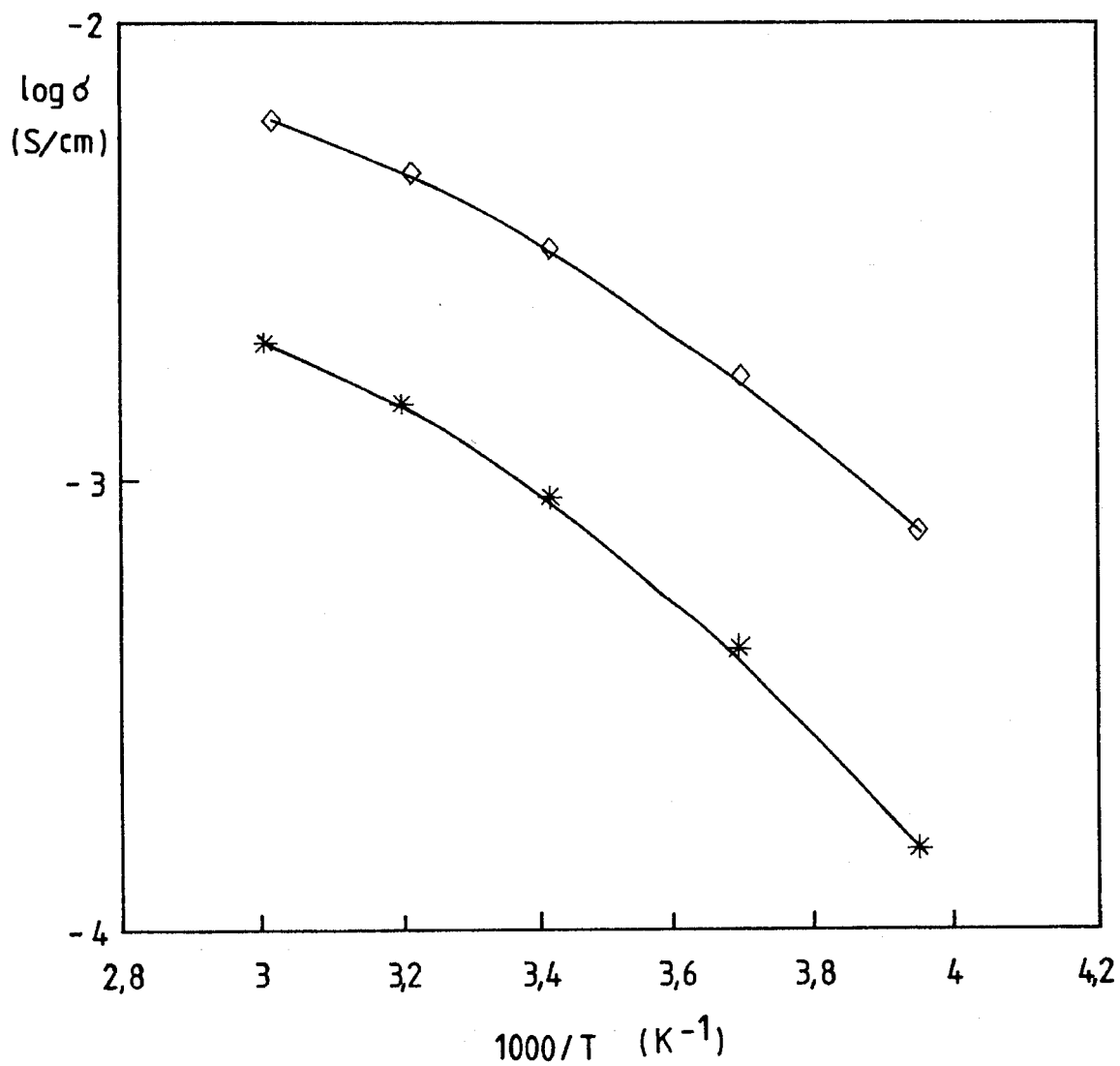

The behaviour of the ionic conductance in relation to the temperature is shown in FIGS. 1 and 2, where the conductance values expressed as S/cm are shown in the ordinate and the temperature values expressed as Kelvin degrees ($1000/T(K^{-1})$) are shown in the abscissa. In particular, in FIG. 1 the curves have the following meaning:
-*-- PVE-SIL (the comparison used is a polyvinylether cross-linked without a plasticizer); --□-- PVE-SIL1; --◊-- PVE-SIL2 and --X-- PVE SIL3. In FIG. 2 --*-- PVE-SIL4 and --◊-- is PVE-SIL5.

We claim:

1. Polymeric electrolyte structure, in the form of a membrane, consisting of a solution of an ion compound in a cross-linked polyether comprising a liquid plasticizer, characterized in that said polymeric electrolyte structure is obtained by the following steps: a) copolymerizing a vinyl ether having the formula:

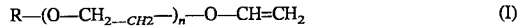

wherein: R indicate the methyl or ethyl radical; n is an integer ranging from 1 to 16; with an allyl vinyl ether having the formula:

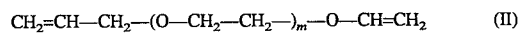

wherein: m is an integer varying from 1 to 10, with a molar ratio between (I) and (II) of between 70/30 and 95/5, to obtain a copolymer having allyl unsaturations; b) hydrosilating the double allyl bond of the copolymer obtained in step (a) by reaction with an alkoxy silane, said silane being trimethoxy or triethoxy silane, to obtain a hydroxylated copolymer;

c) cross-linking the hydrosilated copolymer obtained in step (b) by means of a diprotic cross-linking agent in solution in a plasticizer, said plasticizer being an oligomer or a dipolar aprotic solvent in a quantity of 20 to 80% by weight, in the presence of an ion compound; and evaporating any low-boiling compounds formed in the cross-linking reaction to obtain a membrane capable of containing the liquid plasticizer.

2. Solid polymeric electrolyte according to claim 1, characterized in that in step (a) the copolymer is obtained by cationic polymerization in an inert solvent, at a temperature of about −75° C./−80° C. and in the presence of a Friedel-Crafts catalyst in a quantity of 0.8 to 1.0 moles for every 100 moles of monomers (I) and (II), and the copolymer obtained has a weight average molecular weight of about 20,000–100,000, and a glass transition temperature of −65° C. to −80° C.

3. Solid polymeric electrolyte according to claim 1, characterized in that in step (b) the copolymer prepared in step (a) is reacted with an alkoxy silane operating in solution in an inert and anhydrous solvent, at a temperature of about 80°–100° C. and in the presence of a catalyst containing a transition metal.

4. Solid polymeric electrolyte according to claim 1, characterized in that in step (c) the cross-linking agent is an ethylene glycol acidulated with HCl and added in a quantity of about 40–200 microlitres per gram of copolymer.

5. Solid polymeric electrolyte according to claim 1, characterized in that in step (c) the ion compound is selected from the group consisting of perchlorates, borates, fluoroborates, thiocyahates, hexafluoro arseniates, trifluoroacetates and trifluoromethanesulphonates of the metals lithium, sodium, potassium, calcium, copper, zinc, magnesium, lead, tin and aluminium, in such a quantity as to have an atomic ratio between oxygen in the polyether and metal of about 4/1 to about 18/1.

6. Solid polymeric electrolyte according to claim 5, characterized in that the ion compound is a lithium salt.

7. Solid polymeric electrolyte according to claim 6, characterized in that the lithium salt is lithium perchlorate.

8. Solid polymeric electrolyte according to claim 1, characterized in that in step (c) the plasticizer is an aprotic dipolar solvent selected from the group consisting propylene carbonate, gamma-butyrolactone, ethylene carbonate, dimethoxyethane and mixtures of these.

9. Solid polymeric electrolyte according to claim 1, characterized in that in step (c) the plasticizer is an oligomer selected from oligoethylene glycol dialkylethers and polyethylene glycol dialkylethers.

10. Solid polymeric electrolyte according to claim 1, characterized in that in step (c) the solution is poured into a mould, the low-boiling solvents resulting from the cross-linking reaction are evaporated and the residue is dried until a membrane with a thickness of from 50 to 200 microns is obtained.

11. Solid polymeric electrolyte structure according to claim 1 used as an electrolytic separator in electrochemical devices, in optical and electrochromic displays and in sensors.

* * * * *